United States Patent

De Marchi et al.

[11] Patent Number: 5,940,560
[45] Date of Patent: Aug. 17, 1999

[54] OPTICAL CONNECTION PLUG

[75] Inventors: Silverio De Marchi, Ascona; Silvio Marazzi, Locarno, both of Switzerland

[73] Assignee: Diamond SA, Losone, Switzerland

[21] Appl. No.: 08/937,162

[22] Filed: Sep. 25, 1997

[30] Foreign Application Priority Data

Oct. 28, 1996 [SZ] Swaziland ........................ 2646/96

[51] Int. Cl.⁶ .......................................... G02B 6/38
[52] U.S. Cl. .......................................... 385/58
[58] Field of Search ........................ 385/55, 56, 58, 385/59, 76–79, 139

[56] References Cited

U.S. PATENT DOCUMENTS

| 5,348,487 | 9/1994 | Marazzi et al. | 439/138 |
| 5,363,460 | 11/1994 | Marazzi et al. | 385/70 |
| 5,675,682 | 10/1997 | De Marchi | 385/77 |

FOREIGN PATENT DOCUMENTS 0 613 030 A2  8/1994  European Pat. Off. .

OTHER PUBLICATIONS

Research Disclosure, Mar. 1987, XP 00064534, Fiber Optic Connector with Built–in Shutter, p. 124.

*Primary Examiner*—Akm E. Ullah

[57] ABSTRACT

A protective flap (5) is arranged on the end of a lever arm formed as a flexible spring on the plug casing (2) of a plug (1, 1'), said protective flap covering the face and the end surfaces of an optical fiber. The lever arm is connected to the plug casing so as to be removable, and is shaped and arranged in such a way that the protective flap is pressed against the face under spring tension when in the closed position. With that, the protective flap assumes not only a screening function to guard against the escape of light, but also practically hermetically closes off the face and thus prevents dirt entering between the protective flap and the face.

13 Claims, 5 Drawing Sheets

OPTICAL CONNECTION PLUG

The invention concerns a plug for an optical plug connector according to the preamble to claim 1. The primary purpose of the protective flap covering the face is to protect the end surface of the optical fiber from mechanical interference, and to prevent light from escaping when the plug is disconnected.

BACKGROUND OF THE INVENTION

Protective flaps on optical plugs have been state of the art and in use for some time. With a few state-of-the-art plugs, the protective flap is connected by means of a linkage to the plug housing. This, for example, is the case with the plug disclosed by EP-A-613 030, wherein the plug can be pivoted about lateral bearing pins that snap into mounting bores. On insertion of the plug into a sleeve portion, guide lugs, likewise arranged laterally, run on a guide member on the sleeve portion and so effect the opening movement of the protective flap. This type of protective flap is not suited to all plug connections, and is particularly unsuited to those connections wherein similar plugs are intended for direct pairing without a separate sleeve portion.

"Research Disclosure" (1987), March, No. 275, New York, discloses a related and comparable plug wherein a screen, formed integrally with the plug casing, is displaced laterally during insertion by means of a corresponding control surface. On withdrawal of the plug, the screen springs back due to the elasticity of its material, and covers the face. A disadvantage of this construction is that the screen or protective flap must be manufactured from the same material as the plug housing; it would, however, be desirable for the plug casing to comprise a very hard material in order to hold the optical fiber holder. A further disadvantage of the state-of-the-art construction is that, as a result of the integral formation of the protective flap, the face of the plug is only covered remotely (screening effect) but, for avoidance of a build up of contamination, cannot actually be pressed against the face.

The state-of-the-art plug with protective flaps mostly concern plugs for separate optical fibers only. Recently, however, flat ribbon cables with a plurality of optical fibers have been employed, which require special plugs. In the case of these so-called MT plugs, a plurality of optical fiber end surfaces are arranged on the face in a row. A typical MT plug, for example, is disclosed in EP-A-226 274. Practical protective flaps for MT plugs which open automatically during the plugging sequence are not yet state of the art.

It is therefore a purpose of the invention to create a plug of the type mentioned in the introduction, said plug having a simple construction and wherein the protective flap reliably protects the face from contamination. The construction of the protective flap shall be particularly suited to use on MT plugs for ribbon cable. According to the present invention, this purpose is fulfilled with a plug possessing the features of claim 1.

The arrangement of the lever arm, which is formed as a flexible spring and can be detached from the plug housing, has a plurality of advantages in relation to the state-of-the-art integral form: on the one hand, the same plug housing can be employed without the protective flap, and this is desirable in many applications; on the other hand, the separate arrangement also permits manufacture of the protective flap from a material other than the plug housing, wherein optimal spring properties can be aimed at. In particular, the protective flap can be formed and fixed to the plug casing in such a way that the face is not only covered in the sense of a screen, but the protective flap can also be pressed under spring tension against the face, thus preventing contamination from dust and dirt. For this purpose, the protective flap is pressed under spring tension against the face in the closed position.

Further advantages can be achieved if the face and the inside surface of the protective flap oriented towards said face run at a angle that is offset in relation to a tangent which touches the circle described by the protective flap in the area of the end surface of the optical fiber. With that, the face and the inside surface of the protective flap oriented towards said face can be inclined at 5 to 10°, preferably by approximately 8°, in relation to a plane running at right angles to the optical axis of the optical fiber. With this arrangement, not only pressing of the inside surface of the protective flap against the face of the plug is made possible but, on springing back into the closed position, the protective flap also effects a displacement of contamination on the face in a way that can be compared to a windscreen wiper. With that, it is perfectly conceivable that the face and the inside surface assume slightly different angles in order to enhance this effect.

A particularly simple attachment of the lever arm on the plug casing is attained if said lever is snapped onto the plug casing using a snap engagement means. Accordingly, assembly is considerably facilitated and no further fixation means of any kind such as screws or similar are required.

Preferably, the lever arm and the protective flap are integrally formed from a plastic material, and likewise the plug casing, wherein said plug casing is formed from a plastic material that possesses less elasticity than the plastic material of the lever arm and the protective flap. While the spring properties are in the forefront in the case of the lever arm, the casing shall be mechanically robust and hold the optical fiber precisely. These latter properties require a relatively hard plastic material.

With an MT plug wherein, on the face, the end surfaces of a plurality of optical fibers are arranged in rows, it is particularly advantageous if the protective flap is formed in the shape of a strip and thus simultaneously covers all optical fibers.

In particular in the case of a strip-type form for the protective flap, it is advantageous if the lever arm is formed to be approximately U-shaped, wherein the ends of the U-limbs are snapped into the plug casing and can be pressed toward each another under spring tension for snapping in and removal.

With that, locking tabs or beads can be arranged on the outsides of the ends of the U-limbs which are snapped into recesses on the plug casing. With that, the lever arm with the protective flap forms a type of fork, wherein the fork prongs can be pressed together for insertion into the plug casing. Here, too, the correct choice of elasticity for the material plays a decisive role.

The recesses can be parallel hollow grooves opening towards the face, a locking piece being arranged for security on the plug casing between the U-limbs, said locking piece being gripped to the rear by the inside of the ends of the U-limbs. These openings, recessed and open to one side, can be simply manufactured using injection moulding techniques. The locking piece prevents the U-limbs from sliding out and at the same time serves to orient the positioning of the protective flap.

The opening movement, i.e. pivoting back of the protective flap under spring tension, can be realised in a particularly simple way if the protective flap possesses a run-up surface oriented away from the face, said run-up surface being inclined in such a way that, on running up a ramp on a plug counterpart, the protective flap is pivoted away. The protective flap at the same time thus possesses a control surface for control of the pivoting movement during the plugging sequence. With that, a ramp can additionally be arranged in the area of the face, the protective flap of a similar plug counterpart being pivoted away on said ramp.

Finally, it is also of particular advantage if the ramp blends into a support surface on which the protective flap of a similar plug counterpart rests after reaching the end position. The spring force taking effect on an opposing plug can, in relation to its force direction, thus be deflected in such a way that it does not reduce the force pressing the plugs together. With appropriate shaping of the support surface, it is even conceivable that this pressing force is enlarged still further.

The plug casing can be formed to approximate a cuboid and the pivotable lever arm can be held within the cuboid form within a recess. In this way, the outside dimensions of the plug are not increased by the arrangement of the lever arm. This recessed construction largely prevents unintentional pivoting of the protective flap in the unplugged state.

The individual plugs are preferably formed in such a way that, with a pair of plugs rotated in relation to each other through 180° in relation to the axis of the plugs or the optical axis of the optical fiber, a plug connection can be achieved wherein, with a relative movement of the plugs towards one another, the protective flaps can be pivoted simultaneously in each case by the same components of the opposing plug.

An embodiment of the invention is shown in the drawings and is more precisely described in the following: namely,

DESCRIPTION OF THE PREFERRED EMBODIMENT

Figure 1:
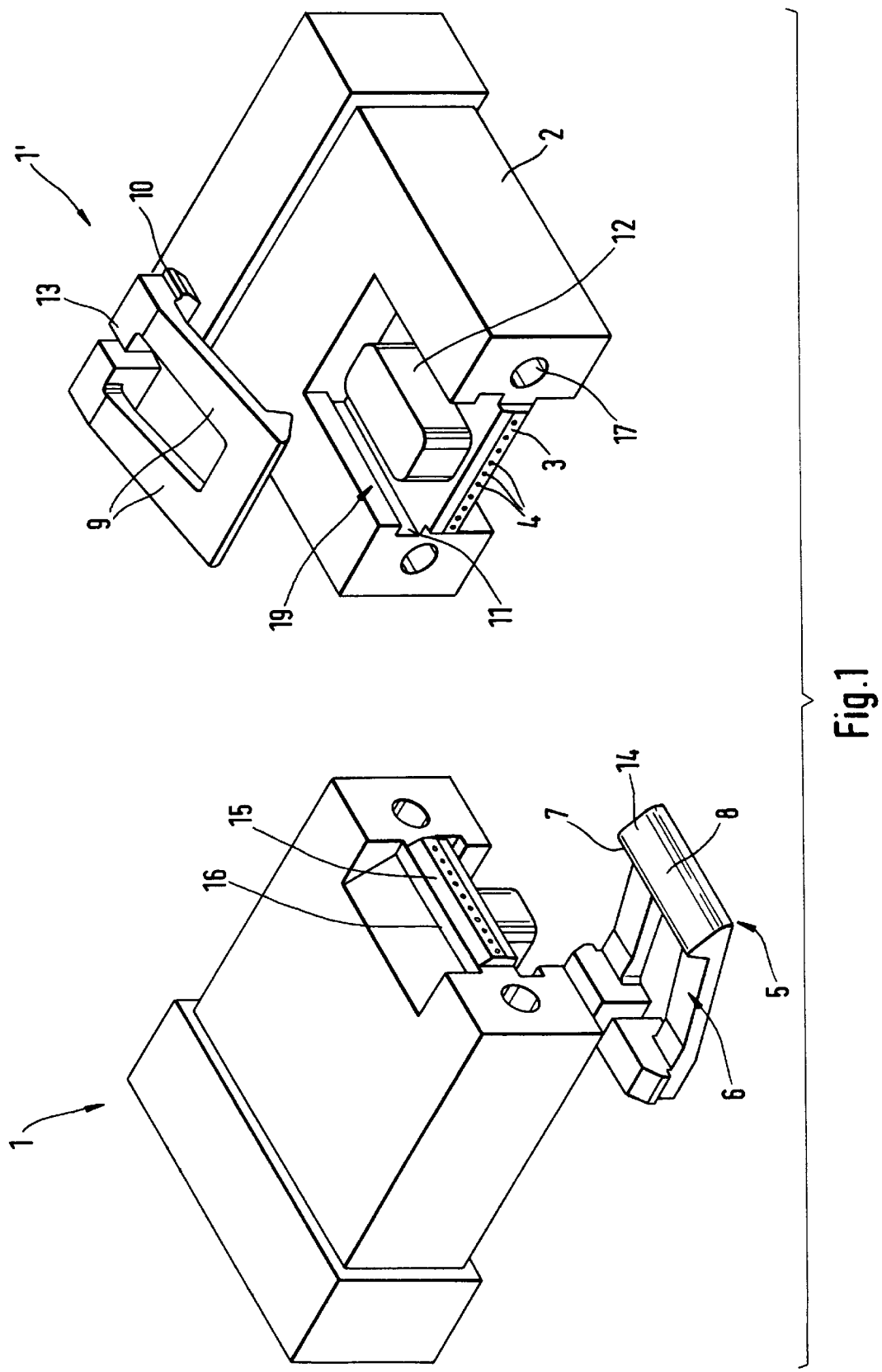
FIG. 1 a perspective view of two plugs rotated in relation to each other by 180°, prior to fitting the protective flaps, FIG. 2 both plugs according to FIG. 1, with protective flaps fitted, FIG. 3 both plugs according to FIG. 2, just before the insertion sequence, FIGS. 4 to 8 cross sections through the plug connection at varying phases of the opening sequence of the protective flap, and FIG. 9 a cross section through the plug casing, showing the geometrical conditions for the face.

As can be seen in FIG. 1, a plug 1 or 1' essentially comprises a plug casing 2, on the face 3 of which the end surfaces of a plurality of optical fibers 4 are arranged and held. An MT plug for ribbon cables is thus concerned, although the present invention is not restricted to this type of plug. The methods of fixing the ribbon cable within the plug casing is known to the expert in the art and will not be more closely described here.

The plug casing is essentially formed as a cuboid and provided with a recess 19 on one side, said recess being open toward the face 3. Hollow grooves 11 are arranged in the side walls of the recess, said hollow grooves also being open toward the face. A locking piece 12 is arranged in the centre of the recess, with the surface of said locking piece being approximately flush with the surface of the plug casing.

Figure 2:
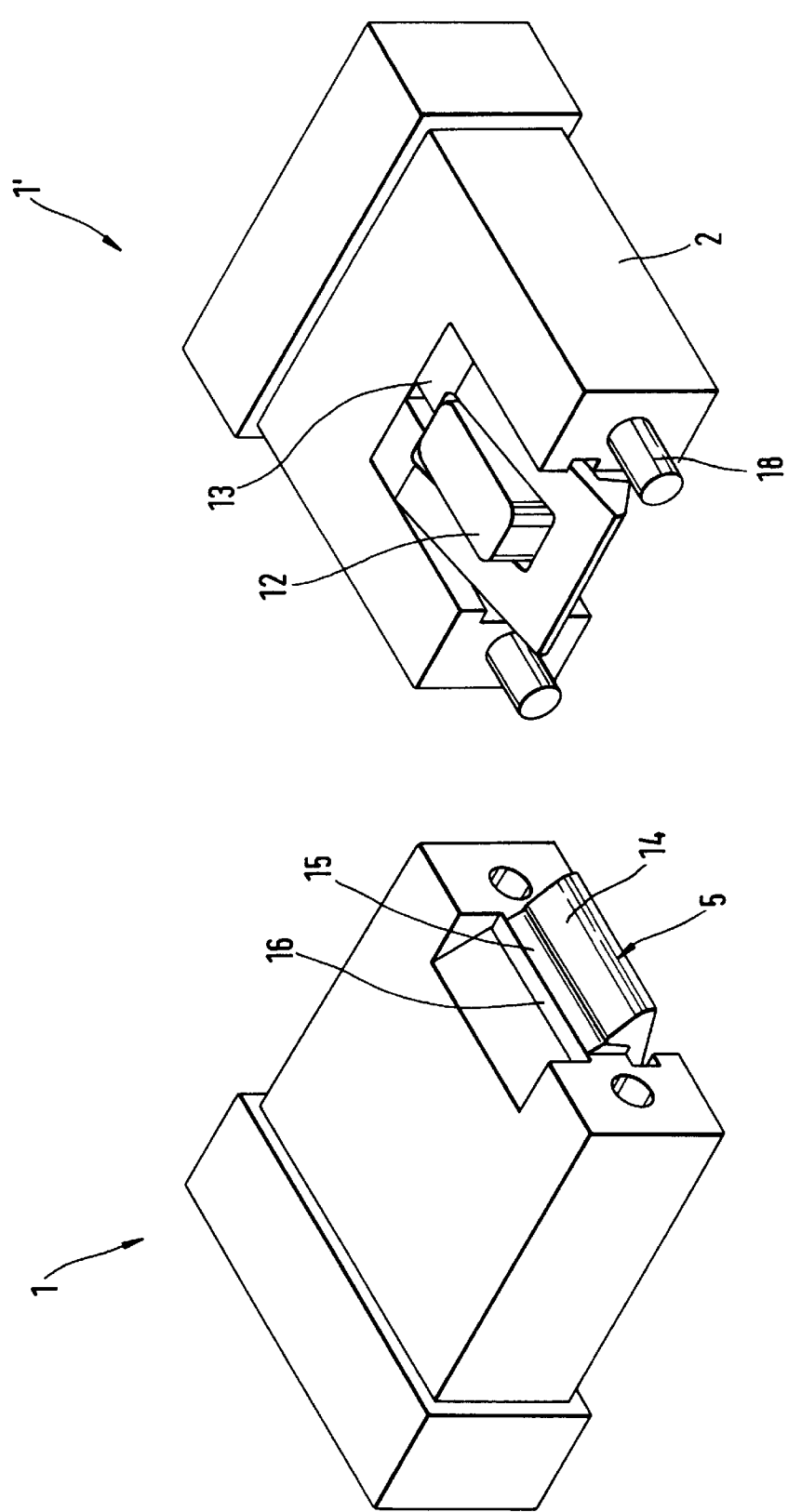

Bores 17 are arranged at each side of and on approximately the same plane as the optical fibers (4), said bores serving to accommodate the centering pins 18 (FIG. 2).

On each plug, a ramp 15 is arranged in the immediate area of the face 3, said ramp blending into a support surface 16. With that, the support surface 16 runs approximately parallel to the plane of the optical fibers.

A protective flap 5 is allocated to each plug, said protective flap essentially being formed as a strip 8 and possessing an inside surface 7 that can be pressed against the face 3. The protective flap is formed integrally with the U-limbs 9 which in entirety form the lever arm 6 about which the protective flap can be pivoted. With that, the lever arm is formed as a flexible spring, although only a section of the lever arm, for example in the area of the snap-in point, can be formed as a flexible linkage.

A run-up surface 14 is arranged on the outside of the strip 8, said run-up surface serving to induce the pivoting movement of the protective flap during the plugging sequence. Locking tabs 10 are arranged laterally on the ends of the U-limbs 9, said locking tabs being able to snap into the lateral hollow grooves 11. On the inside, each U-limb is provided with a locking nose 13 engaging behind the locking piece 12 on the plug casing.

Figure 9:
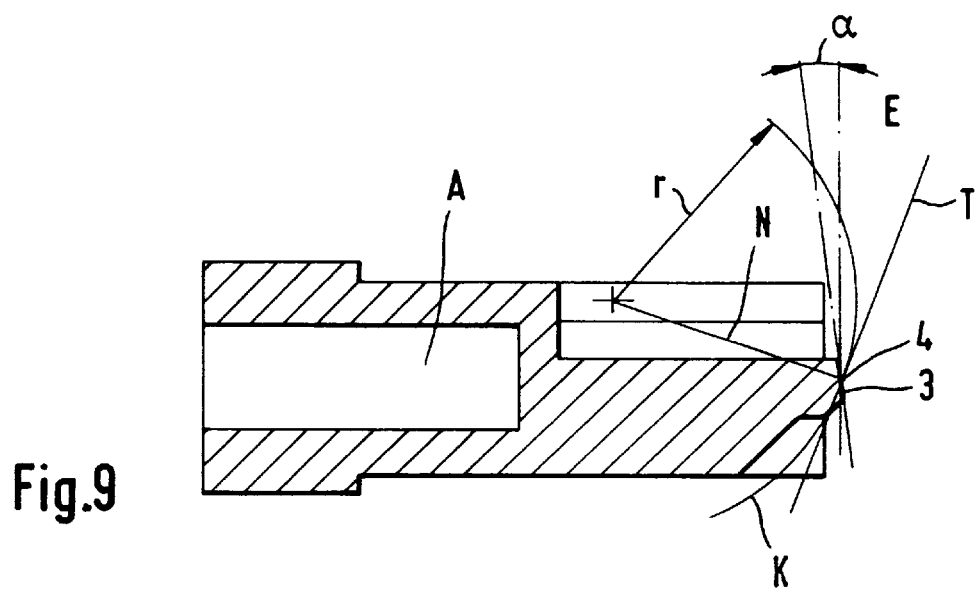

To fit the protective flaps, the U-limbs 9 are pressed slightly together so that the locking tabs 10 snap into the hollow grooves 11. It can be seen in FIG. 2 that in the snapped-in position the U-limbs 9 run at an angle that is inclined in relation to the surface of the plug housing. In this position, in each case the inner surface 7 is pressed under spring tension against the face 3. Details about the geometrical arrangement of the face 3 can be seen in FIG. 9, which shows that the face 3 runs at an angle that is offset in relation to a tangent T, said tangent touching the circle K inscribed by the protective flap in the area of the end surfaces of the optical fibers 4. The vertical N to this tangent thus runs between a virtual point of rotation of the lever arm 6 and the end surfaces of the optical fibers 4. At the same time, however, the face 3 also runs at an inclination in relation to a plane E, said plane E running at a right angle to the optical axis A of the optical fiber 4. The angle of inclination $\alpha$ amounts to 5° to 10°, preferably approximately 8°.

Figure 3:
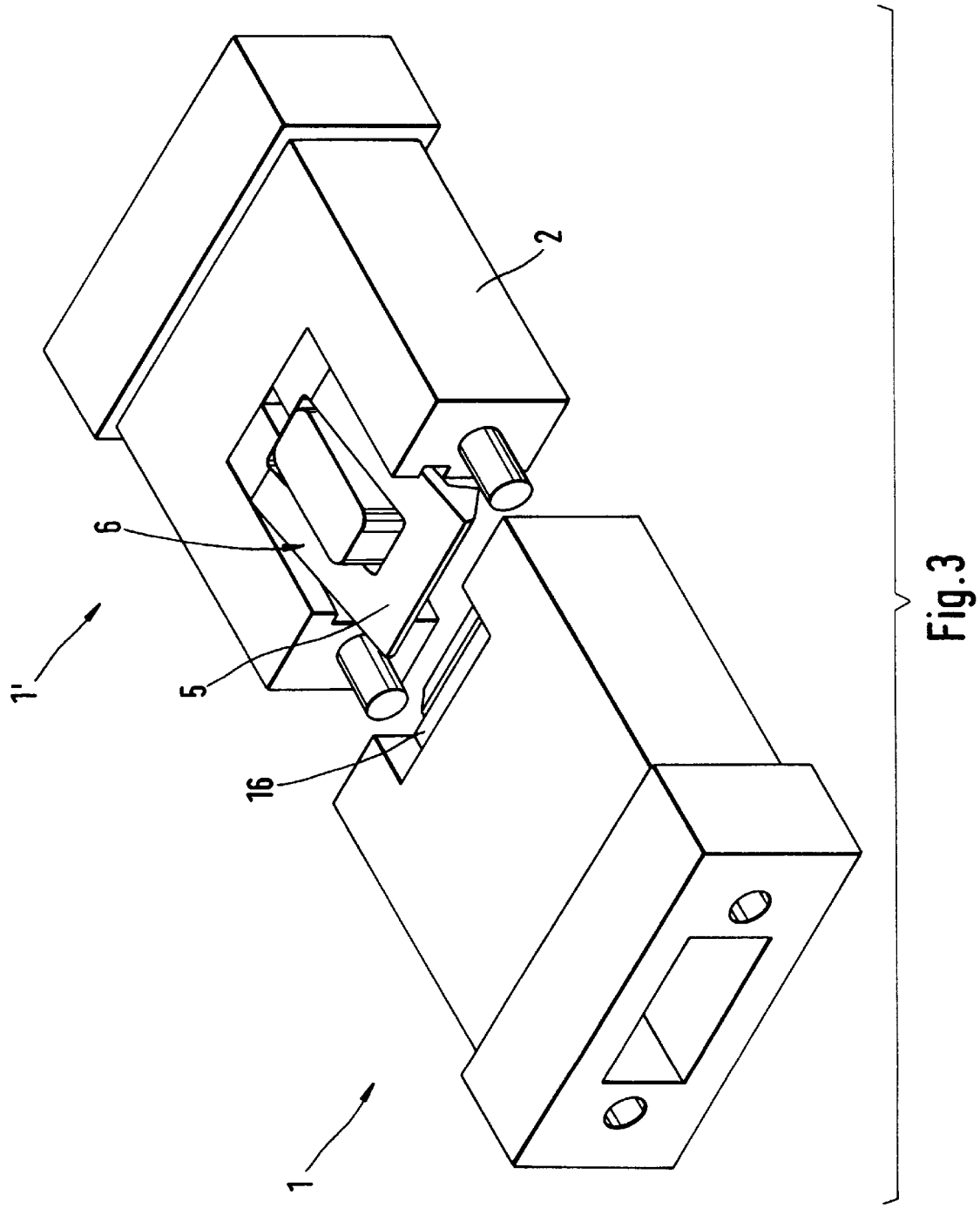
Figure 4:
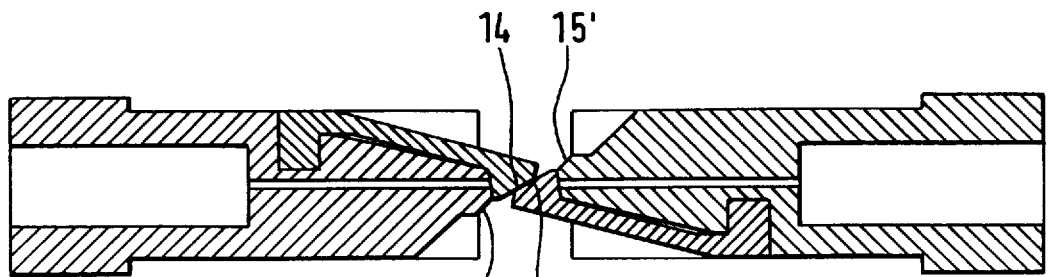

The opening sequence of the protective flaps on plugging two similar plugs together will now be described with reference to FIGS. 4 to 8. With that, the start position is first of all shown in FIG. 3, wherein the centering pins 18 have not yet entered the bores 17 of the opposing plug. After the actual centering sequence, first of all the run-up surfaces 4, 4' of the protective flaps make contact, as shown in FIG. 4.

Figure 5:
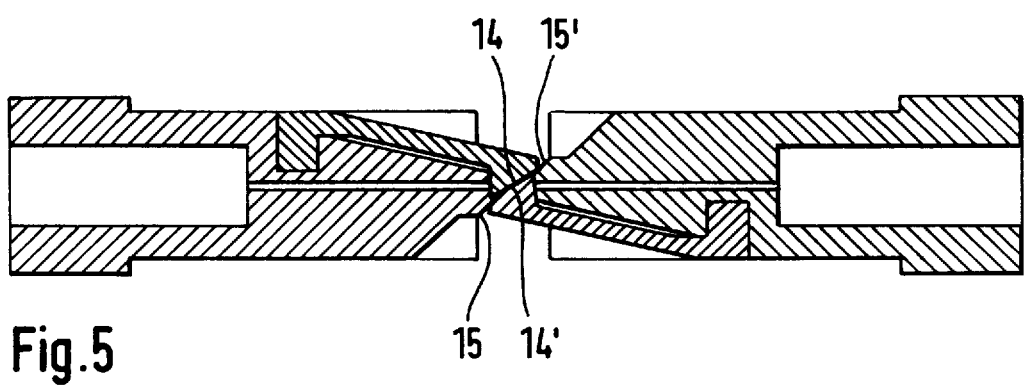

With a further relative movement of both plugs toward each other, the protective flaps start to pivot each other out of the rest position, wherein the run-up surfaces 14, 14' reach the ramps 15, 15' on the respective counterpart. This position is shown in FIG. 5.

Figure 6:
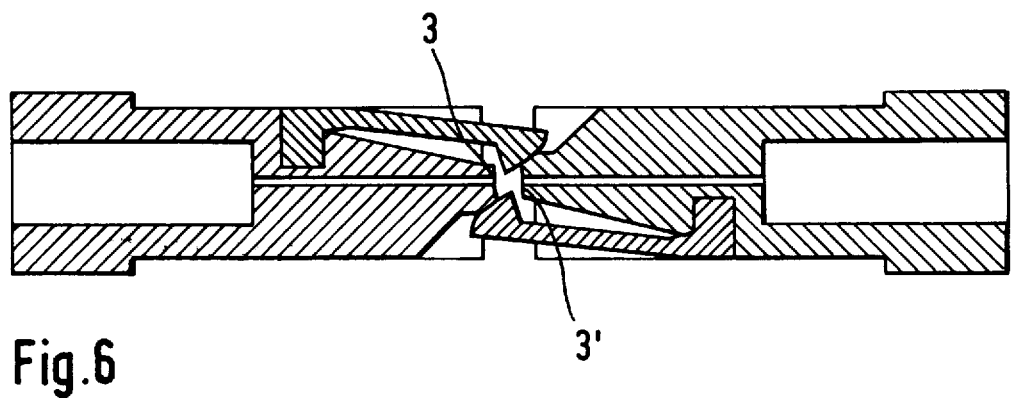
Figure 7:
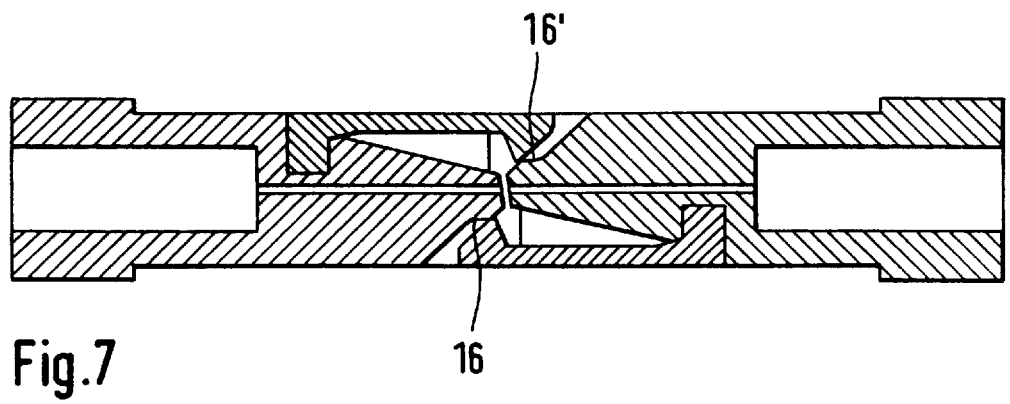

The further pivoting movement now follows exclusively on the ramps, as can be seen in FIG. 6, wherein the screening effect of the protective flaps is now also eliminated.

Figure 8:
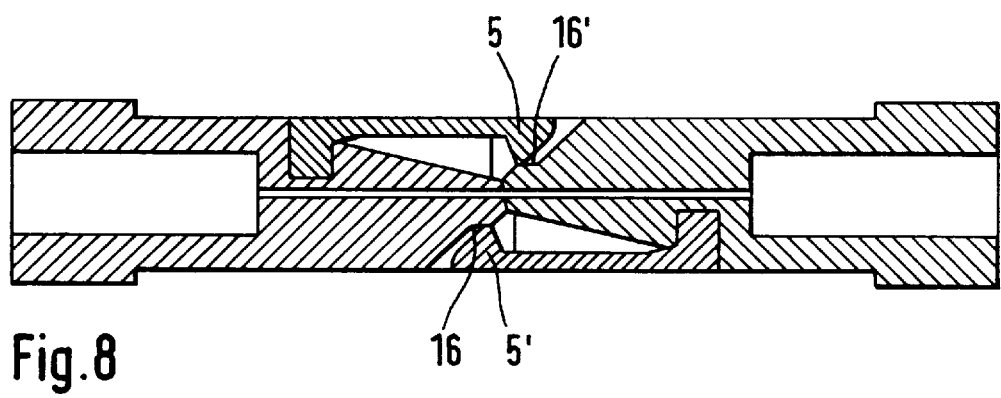

Shortly before the faces 3, 3' make contact, the protective flaps reach the end of the ramps (FIG. 7) and slide onto corresponding support surfaces 16, 16', where they remain, also after the faces have become pressed against each other (FIG. 8). It can be seen from this representation that the spring force on the protective flaps 5 and 5' now takes effect almost at a right angle on the support surfaces 16, 16', and with that, as a result of the inclined position of the faces 3, 3', said faces are pressed against each other. Both the plugs are pressed together in the inserted state by a means not shown here, this pressing force, however, not being reduced or eliminated by the spring force of the protective flaps.

Naturally, alternative embodiments of a protective flap would be conceivable without departing the principle of the invention. For example, separate protective flaps could be arranged on the plug casing for individual optical fibers or groups of optical fibers. It would also be conceivable to pivot the protective flaps away by means other than the guide members on the plug counter part. A separate opening device, in each case requiring manual activation prior to the insertion procedure, would be conceivable.

Inasmuch as the invention is subject to modifications and variations, the foregoing description and accompanying drawings should not be regarded as limiting the invention, which is defined by the following claims and various combinations thereof:

We claim:

1. A optical connection plug (1) comprising
   a casing (2),
   a plurality of optical fibers (4) whose end surfaces are arranged in a row at an end face (3) of said casing, and
   a protective flap (5) covering said face in a closed position, said protective flap being held on the plug casing at one end of a lever arm (6) having a flexible portion acting as a spring so that the protective flap can be pivoted against the spring force away from said closed position, wherein the protective flap is pressed against the face under spring tension, to an open position revealing the face,
   said lever arm having a base which is removably connectable to the plug casing.

2. Plug according to claim 1, characterized in that the face (3) and the inside surface (7) of the protective flap (5) oriented toward said face run offset in relation to a tangential surface (T), said tangential surface touching the circle (K) inscribed by the protective flap (5) in the area of the end surface of the optical fiber (4).

3. Plug according to claim 1, characterized in that the face (3) and the inside surface (7) of the protective flap (5) oriented toward said face is inclined at between 5° and 10°, preferably at approximately 8°, in relation to a plane (E), said plane (E) running at a right angle to the optical axis (A) of the optical fiber.

4. Plug according to claim 1, characterized in that the lever arm (6) is snapped onto the plug casing (2) by means of snap-in means (10).

5. Plug according to claim 1, characterized in that the lever arm (6) and the protective flap (5) are formed integrally from one plastic material and that the plug casing is likewise formed from one plastic material possessing less elasticity that the plastic material of the lever arm and the protective flap.

6. Plug according to claim 1, characterized in that the lever arm (6) is formed as an approximate U-shape, wherein the ends of the U-limbs are snapped into the plug casing (2) and, for snapping in and removal, are pressed together under spring tension.

7. Plug according to claim 6, characterized in that locking tabs (10) or beads are arranged on the outside of the ends of the U-limbs (9), said tabs or beads being able to snap into recesses (11) on the plug casing (2).

8. Plug according to claim 7, characterized in that the recesses are parallel hollow grooves (11) open toward the face (3) and that for security a locking piece (12) is arranged on the plug casing between the U-limbs (9), the rear of said locking piece (12) being gripped by the insides of the ends of the U-limbs.

9. Plug according to claim 1, characterized in that the protective flap (5) possesses a run-up surface (14) on its side oriented away from the face (3), said run-up surface being inclined in such a way that the protective flap (5) is pivoted away on running up a ramp (15) on a plug counterpart.

10. Plug according to claim 9, characterized in that a ramp (15) for pivoting away the protective flap of a similar plug counterpart is arranged in the area of the face (3).

11. Plug according to claim 10, characterized in that the ramp (15) blends into a support surface (16), the protective flap of a similar plug counterpart resting on said support surface after reaching an end position.

12. Plug connection with two similar plugs (1, 1') according to claim 1 wherein, in relation to the axis of the plugs, the plugs are rotated through 180° in relation to each another, and wherein, with a relative movement of the plugs toward one another, the protective flaps are able to be pivoted simultaneously by in each case the same components of the opposing plug.

13. Plug according to claim 1, characterized in that the plug casing (2) is formed to approximate a cuboid and that the pivotable lever arm (6) is held in a recess (19) within the cuboid.

* * * * *